(12) United States Patent
Ritter

(10) Patent No.: US 10,740,900 B2
(45) Date of Patent: Aug. 11, 2020

(54) METHOD FOR OPERATING AN IMAGING X-RAY DEVICE, IN PARTICULAR A COMPUTED TOMOGRAPHY SYSTEM, AN X-RAY DEVICE AND A COMPUTER PROGRAM PRODUCT

(71) Applicant: Siemens Healthcare GmbH, Erlangen (DE)

(72) Inventor: Andre Ritter, Neunkirchen am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 40 days.

(21) Appl. No.: 16/110,228

(22) Filed: Aug. 23, 2018

(65) Prior Publication Data

US 2019/0066302 A1 Feb. 28, 2019

(30) Foreign Application Priority Data

Aug. 29, 2017 (DE) .......................... 10 2017 215 059

(51) Int. Cl.
*G06T 7/11* (2017.01)
*G06T 7/168* (2017.01)
(Continued)

(52) U.S. Cl.
CPC ................ *G06T 7/11* (2017.01); *A61B 6/027* (2013.01); *A61B 6/032* (2013.01); *A61B 6/0407* (2013.01);
(Continued)

(58) Field of Classification Search
CPC ....... A61B 6/027; A61B 6/032; A61B 6/0407; A61B 6/0457; A61B 6/461; A61B 6/469;
(Continued)

(56) References Cited

U.S. PATENT DOCUMENTS 5,805,659 A 9/1998 Tam
6,115,447 A * 9/2000 Hsieh .................. A61B 6/4476
378/19
(Continued)

FOREIGN PATENT DOCUMENTS

CN 107041780 A 8/2017
DE 19742119 A1 4/1998

OTHER PUBLICATIONS

German Office Action 2017P13589 dated May 2, 2018.
(Continued)

*Primary Examiner* — David P Porta
*Assistant Examiner* — Fani Boosalis
(74) *Attorney, Agent, or Firm* — Harness, Dickey & Pierce, P.L.C.

(57) ABSTRACT

A method for operating an imaging X-ray device, and the imaging X-ray device, are disclosed for acquisition of projection images. In an embodiment, X-rays are emitted from at least one X-ray source and, after passing through a tunnel-shaped examination region, acquired by at least one X-ray detector. At least the X-ray source is moved on a circular path or a circular arc section about a center of rotation in a plane of rotation. Herein, a patient couch is moved in a feed direction extending perpendicularly to the plane of rotation. According to at least one embodiment of the invention, a pitch factor is specified characterizing a feed of the patient couch in each unit of time as a function of an at least approximately ascertained position and/or extension of a region to be mapped in the plane of rotation with respect to the center of rotation.

22 Claims, 1 Drawing Sheet

(51) Int. Cl.
  *A61B 6/02*     (2006.01)
  *G06T 11/00*    (2006.01)
  *A61B 6/00*     (2006.01)
  *G06T 7/00*     (2017.01)
  *G06T 7/73*     (2017.01)
  *G06T 3/40*     (2006.01)
  *G06T 7/149*    (2017.01)
  *A61B 6/03*     (2006.01)
  *A61B 6/04*     (2006.01)

(52) U.S. Cl.
  CPC .......... *A61B 6/4078* (2013.01); *A61B 6/5223* (2013.01); *G06T 3/40* (2013.01); *G06T 7/0012* (2013.01); *G06T 7/149* (2017.01); *G06T 7/168* (2017.01); *G06T 7/73* (2017.01); *G06T 11/006* (2013.01); *A61B 6/0457* (2013.01); *A61B 6/461* (2013.01); *A61B 6/469* (2013.01); *A61B 6/488* (2013.01); *G06T 2207/10081* (2013.01); *G06T 2207/20116* (2013.01); *G06T 2207/30004* (2013.01); *G06T 2211/421* (2013.01)

(58) Field of Classification Search
  CPC .................. A61B 6/488; G06T 11/006; G06T 2207/10081; G06T 2207/20116; G06T 2207/30004; G06T 2211/421; G06T 3/40; G06T 7/0012; G06T 7/11; G06T 7/149; G06T 7/168
  See application file for complete search history.

(56) References Cited

U.S. PATENT DOCUMENTS

| | | |
|---|---|---|
| 7,978,810 B2 | 7/2011 | Schwarz et al. |
| 9,247,912 B2 | 2/2016 | Haras et al. |
| 9,402,587 B2 | 8/2016 | Allmendinger et al. |
| 2005/0254621 A1* | 11/2005 | Kalender ............... A61B 6/032 378/46 |
| 2018/0315224 A1 | 11/2018 | Lou et al. |

OTHER PUBLICATIONS

Chinese Office Action and English translation thereof dated Jul. 3, 2019.
German Office Action and English translation thereof dated May 2, 2018.
German Decision to Grant and English translation thereof dated Nov. 14, 2018.

* cited by examiner

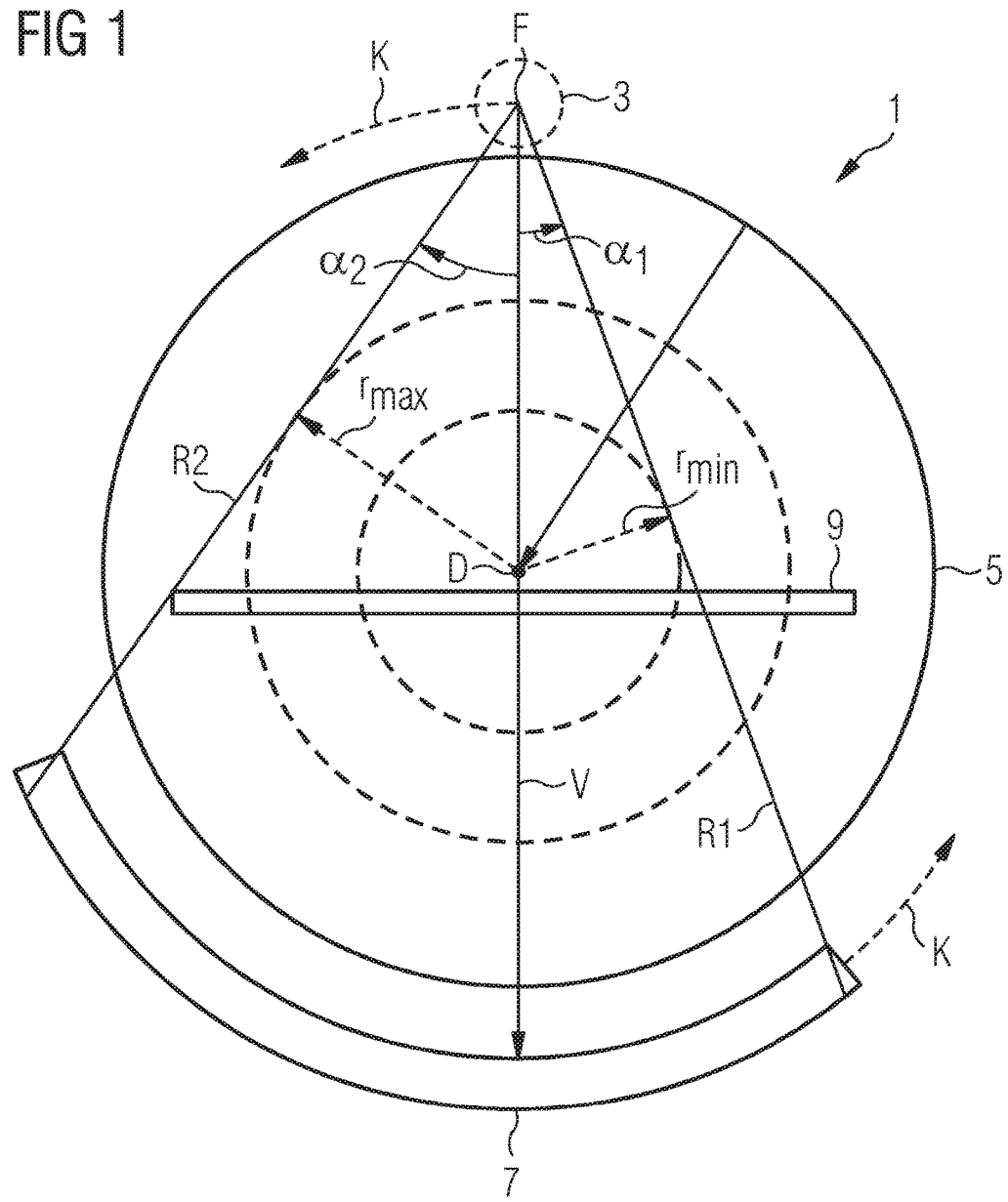
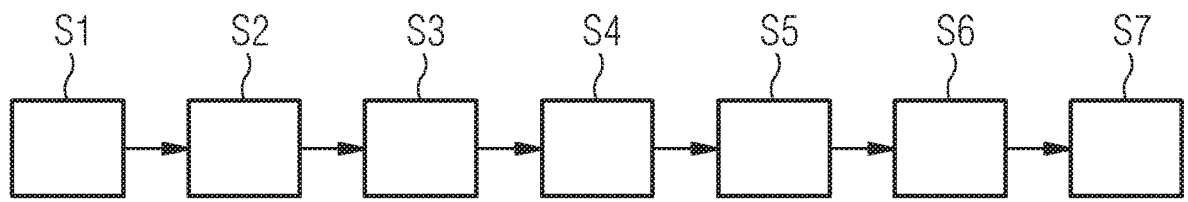

METHOD FOR OPERATING AN IMAGING X-RAY DEVICE, IN PARTICULAR A COMPUTED TOMOGRAPHY SYSTEM, AN X-RAY DEVICE AND A COMPUTER PROGRAM PRODUCT

PRIORITY STATEMENT

The present application hereby claims priority under 35 U.S.C. § 119 to German patent application number DE 102017215059.9 filed Aug. 29, 2017, the entire contents of which are hereby incorporated herein by reference.

FIELD

At least one embodiment of the invention generally relates to a method for operating an imaging X-ray device, in particular a computed tomography system, comprising at least one X-ray source and at least one X-ray detector. For the acquisition of projection images, the at least one X-ray source emits X-rays, which, after passing through a tunnel-shaped examination region, are acquired by at least one X-ray detector. During the acquisition of the projection images, at least the X-ray source is rotated about a center of rotation and a patient couch is moved in a feed direction extending perpendicularly to the rotary motion of the X-ray source.

At least one embodiment of the invention further generally relates to an imaging X-ray device and/or a computer program product, in particular for execution via the imaging X-ray device.

BACKGROUND

Imaging X-ray facilities, such as, for example, computed tomography systems, which are embodied to acquire projection images from the inside of a patient's body are well known from the prior art. For examination, the patient is usually positioned on a patient couch, which is typically moved, in particular in the horizontal direction, during the examination. Herein, a region of the patient to be mapped is introduced into a tunnel-shaped examination region around which at least the X-ray source is rotated during the image acquisition. Known from the prior art are in particular computed tomography systems with stationary X-ray detectors or X-ray detectors that move in synchronism with the X-ray source. In the latter case, the X-ray detector, in particular a multi-line detector, and the X-ray source are arranged diametrically opposite the center of rotation.

In computed tomography, image acquisition is usually performed such that, at least for a part of the X-rayed body region, a complete set of projection images acquired from different directions is available. A complete set of projection images enables a three-dimensional reconstruction via filtered back projection of the mapped region. In particular in spiral computed tomography, the patient couch or the patient table is continuously pushed in the horizontal direction while the X-ray source rotates. The feed in units of the effective detector width in the center of rotation with each rotation is generally called the pitch or pitch factor.

The recording parameters, in particular the pitch factor, limit the size of the field of view containing a complete set of projection images for reconstruction. Furthermore, in particular iterative methods are known that enable reconstruction in fields of view which do not contain complete datasets. However, these methods have drawbacks with respect to the achievable image quality and accuracy of the image values. Moreover, artifacts occur to a greater degree at the transition to the field of view that contains complete projection data.

This is particularly disadvantageous when the projection images or a three-dimensional volume reconstructed from the projection images or image slices of the reconstructed three-dimensional volume are to be used as the basis for planning and/or optimization of subsequent radiotherapy. In this case it is essential that it is possible for organs, in particular high-risk organs, located in the field of view to be acquired, to be segmented or contoured exactly.

U.S. Pat. No. 9,402,587 B2 discloses a method for recording projections during a spiral scan. U.S. Pat. No. 9,247,912 B2 discloses a helix scan method with a pitch of at least three.

U.S. Pat. No. 7,978,810 B2 discloses an imaging method for variable pitch spiral CT.

SUMMARY

At least one embodiment of the invention discloses a method for operating an imaging X-ray device with which the region to be mapped can be depicted with high image quality.

Embodiments of the invention are directed to a method for operating an X-ray device, an X-ray device, a non-transitory computer readable medium and a computer program product.

Advantageous embodiments of the invention are the subject matter of the claims.

In one embodiment, a method includes operating an imaging X-ray device, in particular a computed tomography system, for the acquisition of projection images, in particular for tomographic image reconstruction. Herein, at least one X-ray source emits X-rays, which, after passing through a tunnel-shaped examination region into which typically an examination object has been introduced, are acquired by at least one X-ray detector. During the image acquisition or during the scanning of the examination object, at least the X-ray source is rotated about a center of rotation. To this end, the X-ray source is in particular guided on a circular path or on a circular arc section. The scan or rotary motion of the X-ray source takes place in a plane of rotation. Furthermore, a patient couch is moved in a feed direction extending perpendicularly to the scan or rotary motion of the X-ray source. It is provided according to the invention that a pitch factor characterizing a feed of the patient couch in each unit of time is specified as a function of an at least approximately ascertained position and/or extension of a region to be mapped in the plane of rotation with respect to the center of rotation.

At least one embodiment of the invention further relates to the aforementioned imaging X-ray device, in particular a computed tomography system, which in at least one embodiment, is embodied to carry out at least one embodiment of the above-described method. The X-ray device in particular comprises at least X-ray source for emitting X-rays and at least one X-ray detector for acquiring the emitted X-rays after they have passed through an examination region. The at least one X-ray source can be moved on a circular path or a circular arc section about a center of rotation in a plane of rotation. The patient couch can be moved in a feed direction extending perpendicularly to the plane of rotation.

At least one embodiment of the invention also relates to a computer program product, comprising commands, which, on execution via the imaging X-ray device, carries out the above-described method. The imaging X-ray device is in particular embodied to read out and execute the computer program product. To this end, for example, at least one processor, in particular a control unit of the X-ray device, is provided that executes the commands. In at least one embodiment, the computer program product is, for example, implemented in a non-volatile storage medium of the control unit or an otherwise non-transitory computer readable medium.

BRIEF DESCRIPTION OF THE DRAWINGS

For a further description of the invention, reference is made to the example embodiments shown in the drawings, which show in schematic representations:

FIG. 1: an imaging X-ray device with image acquisition in part fan-shaped geometry in a cross-sectional representation;

FIG. 2: a flowchart of a method for the operation of the X-ray device.

Corresponding parts are given the same reference characters in all the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In one embodiment, a method includes operating an imaging X-ray device, in particular a computed tomography system, for the acquisition of projection images, in particular for tomographic image reconstruction. Herein, at least one X-ray source emits X-rays, which, after passing through a tunnel-shaped examination region into which typically an examination object has been introduced, are acquired by at least one X-ray detector. During the image acquisition or during the scanning of the examination object, at least the X-ray source is rotated about a center of rotation. To this end, the X-ray source is in particular guided on a circular path or on a circular arc section. The scan or rotary motion of the X-ray source takes place in a plane of rotation. Furthermore, a patient couch is moved in a feed direction extending perpendicularly to the scan or rotary motion of the X-ray source. It is provided according to the invention that a pitch factor characterizing a feed of the patient couch in each unit of time is specified as a function of an at least approximately ascertained position and/or extension of a region to be mapped in the plane of rotation with respect to the center of rotation.

At least one embodiment of the invention is based on the knowledge that the size of the field of view that contains a complete set of projection data is a function of the geometry of the fan beam emitted by the X-ray source emitted and recording parameters, in particular the pitch factor. For the purposes of the present specification, a complete set of projection data is available for a field of view if it is possible to map the field of view completely using the acquired projection images via back projection.

A pitch factor for the purposes of the application is considered to be the feed of the patient couch in a direction extending perpendicularly to the scan motion of the X-ray source in each unit of time. The feed direction in particular extends in the horizontal direction. The pitch factor can in particular be stated in units of the effective detector width in the center of rotation with each rotation.

It is generally the case that, the smaller the pitch or pitch factor, the larger the field of view for which the complete set of projection data can be acquired. However, the field of view relevant for the examination is frequently not in the center of rotation or does not extend symmetrically to the center of rotation. In such cases, it can be advisable for the projection images to be acquired in part fan-shaped geometry.

With part fan-shaped geometry, the two fan angles that enclose the two outermost beams of the fan beam in the plane of rotation with the imaginary line between the focus of the X-ray source and the center of rotation are not the same size. In other words, the X-ray source emits a fan beam with an extension that does not extend symmetrically to the center of rotation. The two fan angles produce fields of view of different sizes. The field of view usable for the complete reconstruction generally lies between the two extremes determined by the fan angles.

Part fan-shaped geometry is a design decision that is taken in particular for reasons of cost. This geometry enables larger measuring field regions to be achieved or region to be mapped with the same fan angle. Large measuring field regions are in particular desirable for use in radiotherapy planning. It has been found that full image quality in the large measuring field or for a large region to be mapped can generally only be achieved with a reduced pitch or smaller pitch factor, in particular compared to "full-fan" geometry with an equally large measuring field or region to be mapped. This results in correspondingly longer acquisition times or scan times and is therefore generally also associated with higher loading on the X-ray source or X-ray tube.

It is suggested that the position and/or extension of the region to be mapped be at least approximately ascertained in particular with respect to the center of rotation in the plane of rotation. The pitch factor is then in particular set automatically as a function of the position and/or extension of the region to be mapped. In particular, the pitch factor is set such that the region to be mapped is at least approximately in the region for which the complete set of projection data can be acquired. The user obtains assistance and simplification with the specification of the recording region or field of view. In particular, the increasing complexity with part fan-shaped geometry enables the choice or specification of the field of view to be mapped to be simplified.

Hence, there is generally a relationship between the completeness of the projection data, recording geometry and the pitch or pitch factor. An essential condition for completeness of the projection data is that an image point is covered by projections of a minimum angular range, for example 180°. With a defined fan geometry and pitch or pitch factor, it is possible to determine a path with associated projection angles within the boundaries of the fan beam for each point on a circle around the center of rotation. The maximum radius for the region to be mapped is then in particular determined as defined by this condition.

In cases in which this relationship can be described analytically, it is, for example, provided that it be stored accordingly in an electronics component of the X-ray device by way of numerical methods. Here, it is alternatively conceivable to store a type of lookup table that assigns a maximum pitch or pitch factor to a defined maximum field of view. Herein, it is also conceivable for this lookup table to result in a step-by-step change in the maximum pitch or pitch factor. In other words, only when a certain predefined size of the region to be mapped is fallen below is a higher value for the pitch factor enabled. A further continuous reduction in the region to be mapped does not directly lead to a possible higher permitted pitch value although this would theoretically be possible. Only when the next predefined threshold value for the size of the region to be mapped is reached is the maximum value for the pitch factor increased again. The specific values in these lookup tables can in particular be derived from previous case studies and calculations.

The method suggested by at least one embodiment of the invention can, for example, be implemented in control electronics in a control unit that controls the X-ray device. To this end, the control electronics can in particular comprise at least one processor, integrated circuit, microprocessor, microcontroller and/or microchip.

In one embodiment, it is provided that the pitch factor be specified such that complete three-dimensional reconstruction of the field of view to be mapped via filtered back projection is enabled by way of the acquired projection images.

In one embodiment, a warning signal is output visually or acoustically when the pitch factor or a further recording parameter is subsequently changed by user input such that the field of view to be depicted can no longer be completely reconstructed via filtered back projection. The warning signal is output on the device side for example via a monitor, display or loudspeaker.

The position and/or extension of the region to be mapped is preferably ascertained using a projective overview or topogram acquired via the medical imaging facility. The region to be mapped can in particular contain an organ region of the patient to be recorded.

In one embodiment, it is provided that, to ascertain the position and/or extension of the region to be mapped, anatomical landmarks are automatically identified by way of image recognition and/or an organ of the patient in the overview is segmented, in particular automatically segmented. In other words, the region to be mapped is specified as a function of the size and location of organs to be acquired. The region to be mapped specified in this way is, for example, output visually to the user for checking via a display or monitor. Optionally, suitable user inputs can be used to modify or correct the extension and/or position of the region to be mapped.

In one embodiment, it is provided that organ-specific safety distances are automatically taken into account during the ascertainment of the position and/or extension of the region to be mapped. To this end, organ-specific safety distances are in particular stored in a database.

The ascertained region to be mapped is preferably output visually, in particular via a display unit, in particular the aforementioned display or the monitor.

In one embodiment, it is provided that the size of the region to be mapped is subsequently changed using the visual output, in particular using the overview, via a user input, wherein a warning signal is output visually or acoustically when the region to be mapped has been changed to the extent that, in particular taking into account the specified pitch factor and/or other specified recording parameters, it can no longer be completely reconstructed via filtered back projection. This enables it to be ensured that even subsequent changes made on the user's side are automatically checked for consistency with the specified recording parameters.

In another example embodiment, the position and/or extension of the region to be mapped is ascertained at least approximately using a parameterizable three-dimensional patient model. The parameterizable three-dimensional patient model in particular describes the anatomically correct location and extension of organs of a human in digital form.

The patient model can in particular be parameterized with respect to the body size of the patient and characterizes the distribution of attenuation coefficients typically expected with X-ray acquisition. Compared to methods that provide the acquisition of an overview for this purpose, the at least approximate ascertainment of the position and/or extension of the region to be mapped using the parameterizable three-dimensional patient model has the advantage of reduced radiation exposure, in particular for the patient.

Preferably, the parameterizable three-dimensional patient model is adapted to a location of the patient on the patient couch for the at least approximate ascertainment of the position and/or extension of the region to be mapped. Herein, it is provided that the location of the patient is acquired visually and/or stereoscopically, for example via a corresponding embodied acquisition unit such as, for example, a camera.

The above-described properties, features and advantages of the invention and the manner in which these are achieved will become clearer and more plainly comprehensible in conjunction with the following description of the example embodiments explained in more detail with reference to the drawings.

The method suggested by at least one embodiment of the invention can advantageously also be used in combination with another method for complementing or approximate reconstruction of image data outside the specified region to be mapped, i.e. in a field of view, for which no complete set of projection data is available. Hence, the further method for complementing or approximate reconstruction of image data extends the usable field of view to an extended field of view. Such methods are, for example, known by the terms eFoV (extended field of view) or HDFoV.

Such a combination is in particular advantageous when a previously specified size of the recording region is to be achieved independently of the patient and the available recording geometry. This is, for example, the case in radiotherapy as there, as a rule, a fixed field of view with a size of, for example, 500 mm is to be achieved. As a result of the fan angle, a complete recording region, for example in discrete steps of between 400 mm and 500 mm is available as a function of the pitch factor. In this case, the region to be mapped using the method suggested by the invention is only a subregion that is supplemented with the aid of the further method for complementing or approximate reconstruction to the full field of view. This ensures that high-risk organs can be contoured with the required accuracy and, on the other hand, that a pitch or pitch factor can be selected such that the duration of exposure is preferably minimal.

At least one embodiment of the invention further relates to the aforementioned imaging X-ray device, in particular a computed tomography system, which in at least one embodiment, is embodied to carry out at least one embodiment of the above-described method. The X-ray device in particular comprises at least X-ray source for emitting X-rays and at least one X-ray detector for acquiring the emitted X-rays after they have passed through an examination region. The at least one X-ray source can be moved on a circular path or a circular arc section about a center of rotation in a plane of rotation. The patient couch can be moved in a feed direction extending perpendicularly to the plane of rotation.

At least one embodiment of the invention also relates to a computer program product, comprising commands, which, on execution via the imaging X-ray device, carries out the above-described method. The imaging X-ray device is in particular embodied to read out and execute the computer program product. To this end, for example, at least one processor, in particular a control unit of the X-ray device, is provided that executes the commands. In at least one embodiment, the computer program product is, for example, implemented in a non-volatile storage medium of the control unit or an otherwise non-transitory computer readable medium.

FIG. 1 shows an imaging X-ray device 1, which is in particular embodied as a computed tomography system, in a schematic cross-sectional representation. The X-ray device 1 comprises an X-ray source 3, which, for image acquisition, is guided on a circular path K around a tunnel-shaped examination region 5. An X-ray detector 7 arranged diametrically opposite the X-ray source 3 with respect to the tunnel-shaped examination region 5 is moved simultaneously with the X-ray source 3. The X-ray detector 7 acquires the X-rays emitted by the X-ray source 3 after they have passed through an examination object arranged in the examination region 5 on a patient couch 9.

During the image acquisition, the patient couch 9 is pushed continuously in a perpendicular to the drawing plane, which corresponds to the plane of rotation of the scan motion of the X-ray source and X-ray detector. The feed in each unit of time, in particular in units of the effective detector width in the center of rotation with each rotation is generally called the pitch or pitch factor.

The X-rays emitted by the X-ray source 3 are propagated in form of a fan beam from a focus point F to the X-ray detector 7. The arrangement sketched in FIG. 1 corresponds to part fan-shaped geometry with which the fan beam does not extend symmetrically to the center of rotation D. The two X-ray beams R1, R2 bounding the fan beam each enclose differently sized angles $\alpha_1$, $\alpha_2$ with the connecting line V, which extends through the focus point F and the center of rotation D. Accordingly, the length of radial distance $r_{min}$ of the X-ray beam R1 and the length of radial distance $r_{max}$ of the X-ray beam R2 to the center of rotation D in the plane of rotation are different. Generally, the field of view, for which it is possible to acquire a complete set of projection data, lies between these two extremes and is also determined by the amount of the pitch or pitch factor.

FIG. 2 is a schematic depiction of a flowchart according to a possible example embodiment of the method for operating the X-ray device 1.

Initially, the examination object, which can, in particular, be an organ region of the patient to be acquired, is specified in a first method step S1. Optionally, a list of organs to the contoured or segmented is additionally specified. In practice, this can include the choice of a suitable recording protocol.

As a rule, the organ region is specified by the choice of a recording region on overview output on the user's side. As a rule, this takes place via a corresponding user input. The optional list of the organs to be contoured does not necessarily enable conclusions to be drawn regarding the overall recording region required or region to be acquired, but it is generally possible to assess the minimum necessary size of the corresponding region. The list of organs is, for example, linked to a recording protocol and stored in a database. This, on the one hand, permits standardization and, on the other simplifies the workflow since it is not necessary to recompile the list anew for each recording.

In a second method step S2, a projective overview or a topogram of the imaging X-ray device 1 is generated.

In a third method step S3, anatomical landmarks are identified in the projective overview with the aid of correspondingly embodied image recognition software. Alternatively or additionally, boundaries or outlines of organs are contoured or segmented. Once again, image processing software that is known per se is used for this. The identified, segmented or contoured organ boundaries can additionally be marked on the user's side as a visual aid, for example overview output via a suitable unit such as a display.

In the schematically illustrated example embodiment, the organ boundaries define the location and extension of a region to be mapped that is to be acquired with a high degree of accuracy. Therefore, in a third method step, a position and/or extension of the region to be mapped in the plane of rotation is specified at least approximately, for example using segmented organ boundaries.

Alternatively or additionally, in method steps S2 and S3, the position and/or extension of the region to be mapped can take place approximately using a digital three-dimensional patient model. To this end, it is provided that the location and position of the examination object, in particular the patient, on the patient couch 9 is, for example, acquired visually and/or stereoscopically. The digital patient model can be parameterized and is suitably adapted according to the acquired visual or stereoscopic position or location. It is then possible to ascertain the information regarding the position and/or location of the region to be mapped from the patient model in a similar way.

In a fourth method step S4, the maximum radial distance $r_{max}$ to the center of rotation D is assessed in particular from the identified organ boundaries. Additionally, organ-specific safety distances, which are, for example stored in a database, can be retrieved and taken into account in the further method for, in particular during the determination of recording parameters for the subsequent X-ray image acquisition. Taking account of the safety distance in particular enables the minimal size of the region to be mapped to be assessed. This region to be mapped is, for example, visually superimposed on the overview for checking by the user. Optionally, the user is given the option of processing this identified region to be mapped and in particular changed with respect to its position and/or extension.

In the fourth method step S4, it should in particular be noted that, as a rule, the overview shows a two-dimensional projective illustration of the three-dimensional patient anatomy. This should be taken into account accordingly during the specification of safety distances. Alternatively, it would also for example be possible to use a simplified three-dimensional model of the patient's anatomy and its attenuation properties and to adapt this to the overview using an optimization method.

In a fifth method step S5, restrictions for the recording parameters of the following projective X-ray acquisition are derived using the position and/or extension of the region to be mapped taking account of the recording geometry, in particular the above-described part fan-shaped geometry and taking account of the available reconstruction methods. Here, in particular the aforementioned pitch or pitch factor play a role. The recording parameters are preferably selected such that a set of projection images can be acquired that enables a complete reconstruction of the entire region to be mapped via filtered back projection.

In a sixth method step S6, values for the recording parameters, in particular for the pitch factor, are specified. It is in particular provided that optimum parameter values are automatically suggested and output or displayed on the user's side. The user furthermore has the option of changing these parameter values, in particular the parameter value suggested for the pitch factor. If herein a parameter value is changed such that the prespecified limitations are violated, an appropriate acoustic or visual warning or warning signal is output on the user's side.

The choice of the pitch factor in particular influences the overall duration of the X-ray recording. Herein, longer recording times can have a negative influence on the quality of the acquired projection images since artifacts induced by patient motion can occur.

The actual recording of the projection images, which in particular contain the prespecified region to be mapped is performed in a seventh step. Then, optionally a three-dimensional volume is ascertained from the acquired projection images, in particular via filtered back projection. The image data generated in this way can in particular be provided for contouring organs or other anatomical objects.

Herein, it is for example, possible for the list of organ names to be transmitted to an evaluation unit in which suitable segmentation and/or contouring software is implemented. This results in automatic contouring and/or segmentation of the corresponding organs. Herein, the contouring and/or segmentation is preferably limited to the organs named in the list in order to avoid unnecessary computational effort.

Although the invention has been illustrated and described in greater detail with reference to the referred example embodiments, the invention is not restricted thereby. Other variations and combinations can be derived herefrom by the person skilled in the art without departing from the essential concept of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating an imaging X-ray device for acquisition of a projection image, at least one X-ray source of the imaging X-ray device being configured to emit X-rays, and at least one X-ray detector of the imaging X-ray device being configured to acquire the X-rays after passing through a tunnel-shaped examination region, the at least the X-ray source being movable on a circular path or a circular arc section about a center of rotation in a plane of rotation during acquisition of a projection image, and a patient couch being movable in a feed direction extending perpendicularly to the plane of rotation, the method comprising:

specifying a pitch factor, characterizing a feed movement of the patient couch during the acquisition of the projection image, as a function of an at least approximately ascertained at least one of position and extension of a region to be mapped in a plane of rotation with respect to the center of rotation.

2. The method of claim 1, wherein the pitch factor is specified such that complete three-dimensional reconstruction of a field of view to be mapped via filtered back projection is enabled via the acquisition of the projection image.

3. The method of claim 2, wherein a warning signal is output visually or acoustically, when the pitch factor or a further recording parameter is subsequently changed by user input such that the field of view to be depicted can no longer be completely reconstructed via filtered back projection.

4. The method of claim 2, further comprising:
ascertaining the at least one of position and extension of the region to be mapped, with aid of a projective overview acquirable via the medical imaging facility.

5. The method of claim 4, wherein the ascertaining, of the at least one of position and extension of the region to be mapped, includes
automatically identifying anatomical landmarks via image recognition; and
segmenting an organ of the patient in the projective overview.

6. The method of claim 5, during the ascertaining of the at least one of position and extension of the region to be mapped, organ-specific safety distances are automatically taken into account.

7. The method of claim 1, further comprising:
ascertaining the at least one of position and extension of the region to be mapped, with aid of a projective overview acquirable via the medical imaging facility.

8. The method of claim 7, wherein the ascertaining, of the at least one of position and extension of the region to be mapped, includes at least one of
automatically identifying anatomical landmarks via image recognition; and
segmenting an organ of the patient in the projective overview.

9. The method of claim 8, wherein, during the ascertaining of the at least one of position and extension of the region to be mapped, organ-specific safety distances are automatically taken into account.

10. The method of claim 7, further comprising:
visually outputting the at least one of position and extension of the region to be mapped.

11. The method of claim 10, further comprising:
changing a size of the region to be mapped, visually output, via a user input; and
visually or acoustically outputting a warning signal when the region to be mapped has been changed to an extent that, taking into account at least one of the specified pitch factor and further specified recording parameters, the region to be mapped can no longer be completely reconstructed via filtered back projection.

12. The method of claim 1, wherein the ascertaining of the at least one of position and extension of the region to be mapped includes using a parameterizable three-dimensional patient model, at least for approximation.

13. The method of claim 12, wherein the parameterizable three-dimensional patient model is adapted to a location of the patient on the patient couch, wherein the location of the patient is acquired at least one of visually and stereoscopically.

14. A non-transitory computer readable medium storing program code for carrying out the method of claim 1 when the program code is run on a computer.

15. An imaging X-ray device, further comprising:
at least X-ray source to emit X-rays;
at least one X-ray detector to acquire the emitted X-rays after passing through an examination region, the at least the X-ray source being movable on a circular path or a circular arc section about a center of rotation in a plane of rotation; and
a patient couch, movable in a feed direction extending perpendicularly to the plane of rotation, the imaging X-ray device being configured to
specify a pitch factor, characterizing a feed movement of the patient couch during the acquisition of the projection image, as a function of an at least approximately ascertained at least one of position and extension of a region to be mapped in a plane of rotation with respect to the center of rotation.

16. A method for acquisition of a projection image using an X-ray device including at least one X-ray source configured to emit X-rays and at least one X-ray detector configured to acquire the X-rays, after passing through a tunnel-shaped examination region, the method comprising:
moving the at least one X-ray source on a circular path or a circular arc section about a center of rotation in a plane of rotation during acquisition of the projection image; and
moving a patient couch in a feed direction extending perpendicularly to the plane of rotation, a pitch factor characterizing a feed movement of the patient couch during the acquisition of the projection image, being a function of an at least approximately ascertained at least one of position and extension of a region to be mapped in a plane of rotation with respect to the center of rotation.

17. The method of claim 16, wherein the pitch factor is specified such that complete three-dimensional reconstruction of a field of view to be mapped via filtered back projection is enabled via the acquisition of the projection image.

18. The method of claim 16, further comprising:
ascertaining the at least one of position and extension of the region to be mapped, with aid of a projective overview acquirable via the medical imaging facility.

19. The method of claim 18, wherein the ascertaining, of the at least one of position and extension of the region to be mapped, includes at least one of
automatically identifying anatomical landmarks via image recognition; and
segmenting an organ of the patient in the projective overview.

20. The method of claim 19, wherein, during the ascertaining of the at least one of position and extension of the region to be mapped, organ-specific safety distances are automatically taken into account.

21. The method of claim 18, further comprising:
visually outputting the at least one of position and extension of the region to be mapped.

22. A non-transitory computer readable medium storing program code for carrying out the method of claim 16 when the program code is run on a computer.

\* \* \* \* \*